US011200379B2

(12) United States Patent
Karres et al.

(10) Patent No.: US 11,200,379 B2
(45) Date of Patent: *Dec. 14, 2021

(54) ONTOLOGICALLY DRIVEN PROCEDURE CODING

(71) Applicant: Optum360, LLC, Eden Prairie, MN (US)

(72) Inventors: George Karres, San Diego, CA (US); Destinee Tormey, San Diego, CA (US); Christopher Miller, San Diego, CA (US); Brian Potter, Carlsbad, CA (US); Mark L. Morsch, San Diego, CA (US)

(73) Assignee: Optum360, LLC, Eden Prairie, MN (US)

( * ) Notice: Subject to any disclaimer, the term of this patent is extended or adjusted under 35 U.S.C. 154(b) by 62 days.

This patent is subject to a terminal disclaimer.

(21) Appl. No.: 16/425,391

(22) Filed: May 29, 2019

(65) Prior Publication Data

US 2019/0317995 A1 Oct. 17, 2019

Related U.S. Application Data

(63) Continuation of application No. 16/166,092, filed on Oct. 20, 2018, which is a continuation of application
(Continued)

(51) Int. Cl.
*G06F 40/30* (2020.01)
*G16H 10/20* (2018.01)
(Continued)

(52) U.S. Cl.
CPC ............. *G06F 40/30* (2020.01); *G16H 10/20* (2018.01); *G16H 10/60* (2018.01); *G16Z 99/00* (2019.02)

(58) Field of Classification Search
None
See application file for complete search history.

(56) References Cited

U.S. PATENT DOCUMENTS 3,996,672 A 12/1976 Osofsky et al.
5,307,262 A 4/1994 Ertel
(Continued)

FOREIGN PATENT DOCUMENTS

WO 2004/055783 A2 7/2004
WO 2006/014845 A2 2/2006
(Continued)

OTHER PUBLICATIONS

U.S. Appl. No. 61/850,577, filed Feb. 2012, Martin; kerry.*
(Continued)

*Primary Examiner* — Richa Mishra
(74) *Attorney, Agent, or Firm* — Alston & Bird LLP

(57) ABSTRACT

Computer implemented systems and methods of processing clinical documentation for a multi-axial coding scheme include inputting clinical documentation from memory operatively coupled with a computer system, and executing a natural language processor configured to process narrative text in the clinical documentation. The processor segments the narrative text based on boundaries defined in the clinical documentation, sequences words in the narrative text based on the segmentation, and maps the sequenced words to semantic objects in an ontology database. The ontology defines classes of semantic objects and relationships between them, corresponding to the multi-axial coding scheme. The semantic objects are converted into characters and output into slots in a medical code, with the characters positioned in the slots based on the multi-axial coding scheme.

18 Claims, 7 Drawing Sheets

Related U.S. Application Data

No. 14/043,344, filed on Oct. 1, 2013, now Pat. No. 10,133,727.

(51) Int. Cl.
*G16H 10/60* (2018.01)
*G16Z 99/00* (2019.01)

(56) References Cited

U.S. PATENT DOCUMENTS

| | | | |
|---|---|---|---|
| 5,325,293 A | 6/1994 | Dorne | |
| 5,483,443 A | 1/1996 | Milstein et al. | |
| 5,583,758 A | 12/1996 | McIlroy et al. | |
| 5,594,638 A | 1/1997 | Iliff | |
| 5,619,709 A | 4/1997 | Caid et al. | |
| 5,675,819 A | 10/1997 | Schuetze | |
| 5,680,511 A | 10/1997 | Baker et al. | |
| 5,778,157 A | 7/1998 | Oatman et al. | |
| 5,794,178 A | 8/1998 | Caid et al. | |
| 5,809,476 A | 9/1998 | Ryan | |
| 5,873,056 A | 2/1999 | Liddy et al. | |
| 5,900,871 A | 5/1999 | Atkin et al. | |
| 5,963,894 A | 10/1999 | Richardson et al. | |
| 5,995,955 A | 11/1999 | Oatman et al. | |
| 6,055,494 A | 4/2000 | Friedman | |
| 6,081,774 A | 6/2000 | De et al. | |
| 6,137,911 A | 10/2000 | Zhilyaev | |
| 6,182,029 B1 | 1/2001 | Friedman | |
| 6,389,405 B1 | 5/2002 | Oatman et al. | |
| 6,498,982 B2 | 12/2002 | Bellesfield et al. | |
| 6,529,876 B1 | 3/2003 | Dart et al. | |
| H2098 H | 3/2004 | Morin | |
| 6,708,186 B1 | 3/2004 | Claborn et al. | |
| 6,866,510 B2 | 3/2005 | Polanyi et al. | |
| 6,915,253 B1 | 7/2005 | Chapman | |
| 6,915,254 B1 | 7/2005 | Heinze et al. | |
| 6,980,875 B1 | 12/2005 | Stromberg | |
| 7,043,426 B2 | 5/2006 | Roberge et al. | |
| 7,113,905 B2 | 9/2006 | Parkinson et al. | |
| 7,174,507 B2 | 2/2007 | Baudin et al. | |
| 7,260,480 B1 | 8/2007 | Brown et al. | |
| 7,359,861 B2 | 4/2008 | Lee | |
| 7,360,151 B1 | 4/2008 | Froloff | |
| 7,369,998 B2 | 5/2008 | Sarich et al. | |
| 7,401,077 B2 | 7/2008 | Bobrow et al. | |
| 7,493,253 B1 | 2/2009 | Ceusters et al. | |
| 7,493,326 B2 | 2/2009 | Bishop et al. | |
| 7,516,125 B2 | 4/2009 | Rao et al. | |
| 7,610,190 B2 | 10/2009 | Polanyi et al. | |
| 7,624,027 B1 | 11/2009 | Stern et al. | |
| 7,653,641 B2 | 1/2010 | Theissen et al. | |
| 7,720,723 B2 | 5/2010 | Dicker et al. | |
| 7,725,330 B2 | 5/2010 | Rao et al. | |
| 7,827,165 B2 | 11/2010 | Abernethy et al. | |
| 7,865,358 B2 | 1/2011 | Green et al. | |
| 7,908,552 B2 | 3/2011 | Heinze et al. | |
| 7,949,538 B2 | 5/2011 | Heinze | |
| 8,078,454 B2 | 12/2011 | Pouzin | |
| 8,140,323 B2 | 3/2012 | Johnson et al. | |
| 8,423,370 B2 | 4/2013 | Heinze | |
| 8,438,496 B1 | 5/2013 | Hegde | |
| 8,548,795 B2 | 10/2013 | Anisimovich et al. | |
| 8,655,668 B2 | 2/2014 | Heinze | |
| 8,682,823 B2 | 3/2014 | Heinze et al. | |
| 8,719,703 B2 | 5/2014 | Bier | |
| 8,731,954 B2 | 5/2014 | Heinze et al. | |
| 8,898,798 B2 | 11/2014 | Rogers et al. | |
| 9,110,756 B1 | 8/2015 | Guo et al. | |
| 9,804,772 B2 | 10/2017 | Oh et al. | |
| 10,133,727 B2 | 11/2018 | Karres et al. | |
| 2002/0010714 A1 | 1/2002 | Hetherington | |
| 2002/0035581 A1 | 3/2002 | Reynar et al. | |
| 2002/0085040 A1 | 7/2002 | Krolczyk et al. | |
| 2002/0128819 A1 | 9/2002 | Jessee et al. | |
| 2002/0156810 A1 | 10/2002 | Holland et al. | |
| 2003/0018251 A1 | 1/2003 | Solomon | |
| 2003/0033347 A1 | 2/2003 | Bolle et al. | |
| 2003/0115039 A1 | 6/2003 | Wang | |
| 2003/0115195 A1 | 6/2003 | Fogel et al. | |
| 2003/0217052 A1 | 11/2003 | Rubenczyk et al. | |
| 2004/0059577 A1 | 3/2004 | Pickering | |
| 2004/0064808 A1 | 4/2004 | Kira | |
| 2004/0093293 A1 | 5/2004 | Cheung | |
| 2004/0117206 A1 | 6/2004 | Steinberger et al. | |
| 2004/0117734 A1 | 6/2004 | Krickhahn | |
| 2004/0172297 A1 | 9/2004 | Rao et al. | |
| 2004/0249638 A1 | 12/2004 | Wang | |
| 2004/0254816 A1 | 12/2004 | Myers | |
| 2005/0010421 A1 | 1/2005 | Watanabe et al. | |
| 2005/0071185 A1 | 3/2005 | Thompson | |
| 2005/0091067 A1 | 4/2005 | Johnson | |
| 2005/0137910 A1 | 6/2005 | Rao et al. | |
| 2005/0261910 A1 | 11/2005 | Precoda et al. | |
| 2005/0273361 A1 | 12/2005 | Busch | |
| 2006/0020444 A1 | 1/2006 | Cousineau et al. | |
| 2006/0020447 A1 | 1/2006 | Cousineau et al. | |
| 2006/0020465 A1 | 1/2006 | Cousineau et al. | |
| 2006/0020466 A1 | 1/2006 | Cousineau et al. | |
| 2006/0020492 A1 | 1/2006 | Cousineau et al. | |
| 2006/0020493 A1 | 1/2006 | Cousineau et al. | |
| 2006/0059021 A1 | 3/2006 | Yulman et al. | |
| 2006/0129922 A1 | 6/2006 | Walker | |
| 2006/0134750 A1 | 6/2006 | Liu et al. | |
| 2006/0149565 A1 | 7/2006 | Riley | |
| 2006/0247949 A1 | 11/2006 | Shorrosh | |
| 2007/0061348 A1 | 3/2007 | Holland et al. | |
| 2007/0094030 A1 | 4/2007 | Xu | |
| 2007/0226211 A1 | 9/2007 | Heinze et al. | |
| 2007/0237377 A1 | 10/2007 | Oosawa | |
| 2007/0294200 A1 | 12/2007 | Au | |
| 2008/0004505 A1 | 1/2008 | Kapit et al. | |
| 2008/0222518 A1 | 9/2008 | Walker | |
| 2008/0256108 A1 | 10/2008 | Heinze et al. | |
| 2008/0256329 A1 | 10/2008 | Heinze et al. | |
| 2008/0282153 A1 | 11/2008 | Kindeberg et al. | |
| 2009/0055477 A1 | 2/2009 | Flesher et al. | |
| 2009/0070140 A1 | 3/2009 | Morsch et al. | |
| 2009/0144617 A1 | 6/2009 | Funes et al. | |
| 2009/0175550 A1 | 7/2009 | Taleb | |
| 2010/0064131 A1 | 3/2010 | Spatscheck et al. | |
| 2010/0070517 A1 | 3/2010 | Ghosh et al. | |
| 2010/0082673 A1 | 4/2010 | Nakano et al. | |
| 2010/0195909 A1 | 8/2010 | Wasson et al. | |
| 2010/0257444 A1 | 10/2010 | Bever et al. | |
| 2011/0093479 A1 | 4/2011 | Fuchs | |
| 2011/0167074 A1 | 7/2011 | Heinze et al. | |
| 2011/0307521 A1 | 12/2011 | Slezak et al. | |
| 2012/0011084 A1 | 1/2012 | Gulwani et al. | |
| 2012/0011470 A1 | 1/2012 | Oh et al. | |
| 2012/0014559 A1 | 1/2012 | Suehling et al. | |
| 2012/0060216 A1 | 3/2012 | Chaudhri et al. | |
| 2012/0109994 A1 | 5/2012 | Ju et al. | |
| 2012/0136863 A1 | 5/2012 | Bobick et al. | |
| 2012/0212337 A1 | 8/2012 | Montyne et al. | |
| 2012/0239671 A1 | 9/2012 | Chaudhri et al. | |
| 2012/0278102 A1 | 11/2012 | Johnson | |
| 2013/0006653 A1* | 1/2013 | Mills | G16H 15/00 705/2 |
| 2013/0103615 A1 | 4/2013 | Mun | |
| 2013/0212508 A1 | 8/2013 | Barsoum et al. | |
| 2013/0246480 A1 | 9/2013 | Lemcke et al. | |
| 2013/0262125 A1 | 10/2013 | Tunstall-Pedoe | |
| 2014/0019128 A1 | 1/2014 | Riskin et al. | |
| 2014/0019160 A1 | 1/2014 | Loya et al. | |
| 2014/0074797 A1 | 3/2014 | McFarland | |
| 2014/0074867 A1 | 3/2014 | McFarland | |
| 2014/0129803 A1 | 5/2014 | Heinze et al. | |
| 2014/0164388 A1 | 6/2014 | Zhang et al. | |
| 2014/0257842 A1 | 9/2014 | Heinze et al. | |
| 2014/0337044 A1 | 11/2014 | Heinze | |
| 2015/0066537 A1 | 3/2015 | Sheffer | |
| 2015/0066539 A1 | 3/2015 | Sheffer et al. | |
| 2016/0004825 A1* | 1/2016 | Martin | G16H 10/60 705/3 |

(56) References Cited

U.S. PATENT DOCUMENTS

| | | | |
|---|---|---|---|
| 2017/0046425 | A1 | 2/2017 | Tonkin et al. |
| 2018/0197261 | A1 | 7/2018 | Morsch et al. |
| 2018/0293071 | A1 | 10/2018 | Heinze et al. |
| 2018/0341636 | A1 | 11/2018 | Heinze et al. |
| 2019/0057083 | A1 | 2/2019 | Karres et al. |

FOREIGN PATENT DOCUMENTS

| | | |
|---|---|---|
| WO | 2006/014846 A2 | 2/2006 |
| WO | 2006/014847 A2 | 2/2006 |
| WO | 2006/014851 A1 | 2/2006 |
| WO | 2012/122122 A1 | 9/2012 |

OTHER PUBLICATIONS

Gergely He'jaa,*, Gyo rgy Surja'nb, Gergely Luka' csyc, Pe'ter Pallinger a, Miklo's Gergelyb; GALEN based formal representation of ICD10; Pages: all URL: https://www.sciencedirect.com/science/article/pii/S1386505606001997 (Year: 2007).*
BR Office Action dated Mar. 3, 2020 for BR Application No. 112016007163.
Final Rejection dated Feb. 19, 2016 for U.S. Appl. No. 14/043,344.
Final Rejection dated Mar. 2, 2017 for U.S. Appl. No. 14/043,344.
Non-Final Rejection dated Aug. 14, 2015 for U.S. Appl. No. 14/043,344.
Non-Final Rejection dated Jul. 14, 2017 for U.S. Appl. No. 14/043,344.
Non-Final Rejection dated Mar. 8, 2018 for U.S. Appl. No. 14/043,344.
Non-Final Rejection dated Sep. 23, 2016 for U.S. Appl. No. 14/043,344.
Notice of Allowance and Fees Due (PTOL-85) dated Aug. 15, 2018 for U.S. Appl. No. 14/043,344.
Notice of Allowance and Fees Due (PTOL-85) dated Jul. 13, 2018 for U.S. Appl. No. 14/043,344.
Raghav Bharadwaj, Artificial Intelligence for Medical Billing and Coding, Mar. 16, 2018, 38 pages, https://www.techemergence.com/artificial-intelligence-medical-billing-coding/, Aug. 2, 2018.
Richard Wolniewicz, PhD, Computer-assisted coding and natural language processing, copyright 2015, 3M Health Information Systems, 12 pages, https://static1.squarespace.com/static/57302e3040261d2ef98c91c0/t/573c13b81d07c003b4e2a430/1463555008957/3M_NLP_white_paper.pdf, Feb. 26, 2019.
"SNOMED CT Browsers," U.S. Department of Health & Human Services, (article), (online), (3 pages), [retrieved from the Internet Sep. 29, 2019] <https://www.nim.nih.gov/research/umls/Snomed/snomed_browsers.html>.
"Supercharged CDI: NLP, Intelligent Workflow and CAC Revolutionize CDI Program at UPMC," OPTUM, White Paper, Mar. 2013, (6 pages).
Aronow, David B. et al. "A PC Classifier of Clinical Text Documents: Advanced Information Retrieval Technology Transfer," Conference entitled American Medical Informatics Association: Beyond the Superhighway; Exploiting the Internet With Medical Informatics—Annual Fall Symposium, AMIA Annual Symposium, p. 932, Hanley & Belfus (1996).
Aronow, David B. et al. "Ad-Hoc Classification of Electronic Clinical Documents," D-Lib Magazine, Jan. 1997, pp. 1-8, Amherst, MA. [retrieved from the Internet Sep. 19, 2019] <URL: <http://www.dlib.org/dlib/January97/medica1/01aronow.html>.
Aronow, David B. et al. "Automated Identification of Episodes of Asthma Exacerbation for Quality Measurement in a Computer-Based Medical Record," Proceedings of the Annual Symposium on Computer Application in Medical Care, American Medical Informatics Association, Brookline, MA, pp. 309-313 (1995).
Corley Courtney et al. "Measuring the Semantic Similarity of Texts," Proceedings of the ACL Workshop on Empirical Modeling of Semantic Equivalence and Entailment, ACM 2005, pp. 13-18.
Department of Health and Human Services, "HIPPA Administrative Simplifications: Modification to Medical Data Code Set Standards to Adopt ICD-10-CM and ICD-10-PCS," Federal Register vol. 74, No. 11, Jan. 16, 2009/Rules and Regulations, (35 pages).
Department of Health and Human Services—OIG Office of Audit Services. Rat-Stats User Guide, Sep. 2001, (108 pages).
Endicott, Melanie. "Innovations in CDI Automation," ICD-TEN Top Emerging News, May 2013, (2 pages).
Furuse, Osamu et al. "Constituent Boundary Parsing for Example-Based Machine Translation," Google 1994, pp. 105-111.
Giunchiglia, Fausto et al. "Approximate Structure-Preserving Semantic Matching," In OTM Confederated International Conferences, On the Move to Meaningful Internet Systems, pp. 1217-1234, (2008). Springer, Berlin, Heidelberg.
Heja, Gergely et al. "GALEN Based Formal Representation of ICD10," International Journal of Medical Informatics, Elsevier Scientific Publishers, Shannon, IR, vol. 76, No. 2-3, Feb. 10, 2007, pp. 118-123.
Hirsch, Morris et al. "Suggesting Terms for Query Expansion in a Medical Information Retrieval System", AMIA Annual Symposium on Computer Application in Medical Care, 1995, p. 965.
International Searching Authority, International Search Report and Written Opinion for International Application No. PCT/US2014/054329, dated Feb. 3, 2015, (11 pages), Rijswijk, The Netherlands.
International Searching Authority, International Search Report and Written Opinion, for International Application No. PCT/US2014/058538, dated Feb. 4, 2015, (11 pages), Rijswijk, The Netherlands.
Jorg, Brigitte et al. Modeling the Semantics of Contextual and Content-Specific Research Metadata Using Ontology Languages: Issues on Combining CERIF and OWL, Procedia Computer Science, vol. 9, Elsevier 2012, pp. 1563-1570.
Larkey, Leah S. et al. "Automatic Assignment of ICD9 Codes to Discharge Summaries," Technical Report, IR-64, Center for Intelligent Information Retrieval, (24 pages), University of Massachusetts, Amherst, MA (1995).
Lehnert, Wendy et al. "Inductive Text Classification for Medical Applications," Journal for Experimental and Theoretical Artificial Intelligence, vol. 7, No. 1, Jan. 1995, (39 pages).
Lenert, Leslie A. et al. "Automated Linkage of Free-Text Descriptions of Patients With a Practice Guideline," Proceedings of the Annual Symposium on Computer Application in Medical Care, pp. 274-278, (1993), American Medical Informatics Association.
Libicki, Martin et al. "The Costs and Benefits of Moving to the ICD-10 Code Sets," Technical Report, RAND Science and Technology, Mar. 2004, Santa Monica, CA. (85 pages).
Morsch, Mark. "Better Technology Leads to Better coding", Optum, White Paper, (2012), (4 pages), Eden Prairie, MN.
Mullin, Robert. "A Brief History of ICD-10-PCS", Journal of AHIMA, vol. 70, No. 9 (1999), (3 pages).
Neubauer, Aljoscha Steffen. "The EWMA Control Chart," Clinical Chemistry, vol. 43, No. 4, pp. 594-601, (1997).
Ranum, David L. "Knowledge Based Understanding of Radiology Text," 12th Annual Symposium on Computer Application in Medical Care, pp. 141-145, (1988), Rochester Minnesota.
Richardson, Stephen D. et al. "MindNet: Acquiring and Structuring Semantic Information From Text," InProceedings of the 36th Annual Meeting of the Association for Computational Linguistics and 17th International Conference on Computational Linguistics—vol. 2, Aug. 10, 1998, pp. 1098-1102, Association for Computational Linguistics.
Robert E. Nolan Company, "Replacing ICD-9-CM with ICD-10-CM and ICD-10-PCS: Challenges, Estimated Costs and Potential Benefits", Oct. 2003. (39 pages), Simsbury, Connecticut and Dallas, Texas.
Sager, Naomi et al. "Automatic Encoding Into SNOMED III: A Preliminary Investigation," 18th Annual Symposium on Computer Application in Medical Care, pp. 230-234, (1994), New York, NY.
Sager, Naomi et al. "Natural Language Processing and the Representation of Clinical Data," Journal of the American Medical Information Association, vol. 1, No. 2, pp. 142-160, Mar./Apr. 1994, New York, NY.
Shaikh, Mostafa Al Masum et al. "Assessing Sentiment of Text by Semantic Dependency and Contextual Valence Analysis," International Conference on Affective Computing and Intelligent Interaction, Sep. 12, 2007, pp. 191-202, Springer, Berlin, Heidelberg.

(56) References Cited

OTHER PUBLICATIONS

Sneiderman, Charles A. et al., "Finding the Findings: Identification of Findings in Medical Literature Using Restricted Natural Language Processing," In Proceedings of the AMIA Annual Fall Symposium, pp. 239-243, (1996), American Medical Informatics Association, National Library of Medicine, Bethesda, MD.

SNOMED—5 Step Briefing, SNOMED International, (2 pages), (online), [retrieved from the Internet Sep. 19, 2019] <https://www.snomed.org/snomed-ct/five-step-briefing>.

SNOMED Clinical Terms User Guide, Jan. 2010 International Release (US English), International Health Terminology Standards Development Organisation, (99 pages), [retrieved from the Internet Jan. 22, 2020] <https://confluence.ihtsdotools.org/download/attachments/18780048/UserGuide_Current-en-US_INT_20100131-significant-changes.pdf?api=v2>.

Soderland, Stephen et al. "Machine Learning of Text Analysis Rules for Clinical Records," Technical Report, TE-39, (5 pages), (1995), Department of Computer Science, University of Massachusetts.

Starosta, Stanley et al. "Lexicase Parsing: A Lexicon-driven Approach to Syntactic Analysis," In Coling 1986 vol. 1: The 11th International Conference on Computational Linguistics, 127-132, (1986).

Stoica, Emilia et al. "Nearly-Automated Metadata Hierarchy Creation," In Proceedings of HLT-NAACL 2004: Short Papers, (2004), pp. 117-120.

Varelas, Giannis et al. "Semantic Similarity Method in WordNet and Their Application to Information Retrieval on the Web," Proceedings of the 7th Annual ACM International Workshop on Web Information and Data Management, Jun. 30, 2005, (75 pages).

Wattenberg, Martin et al. "The Word Tree, An Interactive Visual Concordance," IEEE Transactions on Visualization and Computer Graphics, vol. 14, No. 6, Nov./Dec. 2008, pp. 1221-1228.

Yang, Yiming et al. "An Application of Least Squares Fit Mapping to Clinical Classification," 16th Annual Symposium on Computer Application in Medical Care, pp. 460-464, (1993), Rochester, Minnesota.

Zhou, Xiaohua et al. "Converting Semi-structured Clinical Medical Records Into Information and Knowledge," Proceedings of the 21st International Conference on Data Engineering (ICDE '05), IEEE 2005, (8 pages).

"Using Coding Automation to Aid the Transition to ICD-10," Educational Report Sponsored by Optum, HFMA Healthcare Financial Management Association, pp. 1-8, Nov. 2011.

"Value Proposition for SNOMED CT," International Health Terminology Standards Development Organisation, (2 pages), (online), [Retrieved from the Internet Dec. 21, 2010] <www.ihtsdo.org/fileadmin/user.sub.—upload/Docs.sub.—01/Publications/SNO-MED.sub.—CT/SNOMED.sub.—CT.sub.--Benefits.sub.--v4.pdf>.

Aronow David B. et al. "Automated Classification of Encounter Notes in a Computer Based Medical Record," MEDINFO, 8 part 1, pp. 8-12, (1995).

Croft, W.B. et al. "Effective Access to Distributed Heterogeneous Medical Text Databases," MEDINFO, 8 Part 2, p. 1719, (1995).

Friedman, Carol et al. "Natural Language Processing in An Operational Clinical Information System," Natural Language Engineering, vol. 1, No. 1, pp. 83-108, Mar. 1995.

Gregory, Tom. "Interpreting Error Rates in Health Care Billing Audits," Journal of Health Care Compliance, vol. 5, No. 1, pp. 4-8, Jan.-Feb. 2003.

Johnson, Kerry. "Revenue Cycle Strategist Implementing ICD-10: A Canadian Perspective from the Front Line," Healthcare Financial Management Association, (8 pages), Feb. 2009.

Morsch, Mark et al. "Transitioning to ICD-10: Why You Can Trust NLP Technology With ICD-10 Coding," California Health Information Association 2013 Convention & Exhibit, pp. 1-30, Jun. 11, 2013.

Morsch, Mark. "Advanced Coding Technology to Advance the Revenue Cycle, Natural Language Processing With LifeCode," OptumInsight, pp. 1-4, (2011), Eden Prairie, MN.

Spackman, Kent, "SNOMED Clinical Terms Fundamentals," International Health Terminology Standards Development Organisation, (56 pages), Dec. 14, 2007, (online), [Retrieved from the Internet Dec. 21, 2010] <www.ihtsdo.org/fileadmin/user.sub.—upload/docs.sub.--01/SNOMED.sub.—Cli-nical.sub.—Terms.sub.—Fundamentals.pdf>.

Zingmond, David et al. "Monitoring Free-Text Data Using Medical Language Processing," Computers and Biomedical Research, vol. 26, pp. 467-481, (1993), Stanford, CA.

"HL7 Clinical Document Architecture, Release 2.0," (190 pages), (online) [retrieved from the Internet Jan. 23, 2020] <http://xml.coverpages.org/CDA-20040830v3.pdf>.

"RAT-STATS 2010 Companion Manual, Version 1," Department of Health and Human Services , Office of Inspector General, Office of Audit Services, May 2010, (245 pages).

"RAT-STATS 2010 User Guide, Version 1," Department of Health and Human Services—Office of Inspector General, Office of Audit Services, May 2010, (394 pages).

"Supercharged CDI: NLP, Intelligent Workflow and CAC Revolutionize GDI Program at UPMC," OPTUM, White Paper, Mar. 2013, (6 pages).

United States Patent and Trademark Office, NonFinal Office Action for U.S. Appl. No. 16/166,092, dated Oct. 27, 2020, (77 pages), U.S.

United States Patent and Trademark Office, Final Office Action for U.S. Appl. No. 16/166,092, dated May 19, 2021, (16 pages), USA.

\* cited by examiner

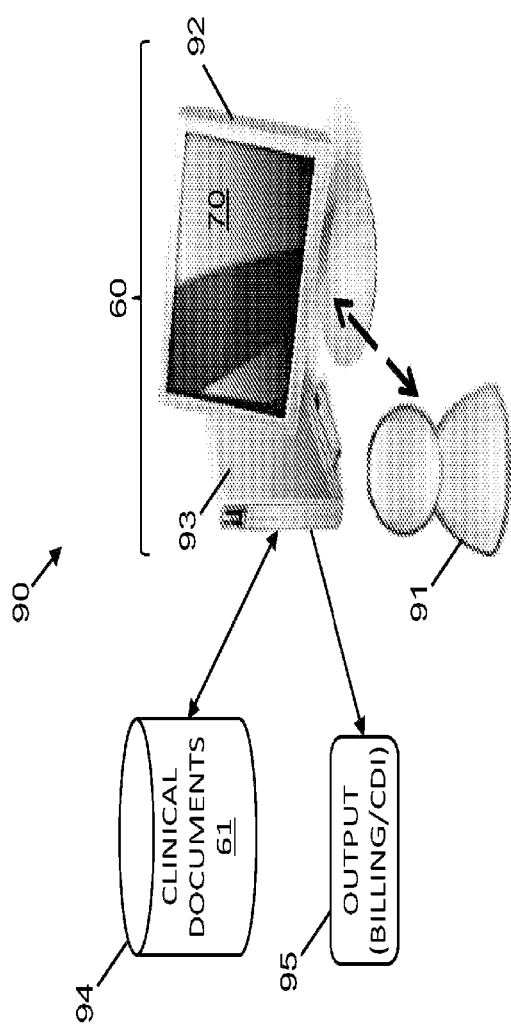

ONTOLOGICALLY DRIVEN PROCEDURE CODING

CROSS-REFERENCE TO RELATED APPLICATIONS

This patent application is a continuation of U.S. patent application Ser. No. 16/166,092, filed Oct. 20, 2018, which is a continuation of U.S. patent application Ser. No. 14/043,344, filed Oct. 1, 2013 and now issued as U.S. Pat. No. 10,133,727, each of which are incorporated herein by reference in its entirety This application is related to the following U.S. patent applications and issued patents, which describe relevant technology. Each of these is incorporated by reference herein, in the entirety and for all purposes: U.S. patent application Ser. No. 09/364,930, AUTOMATICALLY ASSIGNING MEDICAL CODES USING NATURAL LANGUAGE PROCESSING, filed Jul. 30, 1999, issuing Jul. 5, 2005 as U.S. Pat. No. 6,915,254; U.S. patent application Ser. No. 11/735,278, MERE-PARSING WITH BOUNDARY AND SEMANTIC DRIVEN SCOPING, filed Apr. 13, 2007, issuing Mar. 15, 2011 as U.S. Pat. No. 7,908,552; U.S. patent application Ser. No. 13/016,764, MERE-PARSING WITH BOUNDARY AND SEMANTIC DRIVEN SCOPING, filed Jan. 28, 2011; U.S. patent application Ser. No. 11/735,264, MULTI-MAGNITUDINAL VECTORS WITH RESOLUTION BASED ON SOURCE VECTOR FEATURES, filed Apr. 13, 2007; U.S. patent application Ser. No. 12/185,754, VISUALIZING THE DOCUMENTATION AND CODING OF SURGICAL PROCEDURES, filed Aug. 4, 2008; and U.S. patent application Ser. No. 14/019,489, AUTOMATED CLINICAL INDICATOR RECOGNITION WITH NATURAL LANGUAGE PROCESSING, filed Sep. 5, 2013.

BACKGROUND

This disclosure relates generally to clinical documentation, and specifically to improvements in medical coding. In particular, the disclosure relates to ontologically driven medical coding systems and related methods, including compositional natural language processing (NLP) techniques for ICD type (International Classification of Diseases) coding standards, and other medical coding systems. Applications include computer assisted coding (CAC) for medical conditions and treatments, for example procedural coding systems for billing, diagnostic, statistical and analytic purposes.

The ICD coding system was developed in order to provide a standard tool for epidemiology and health care management, including clinical and hospital services. ICD classifications encompass a range of medical conditions including diseases and other disorders, as well as other, more nuanced factors including symptoms, complaints, abnormal findings, external causes of injury or disease, and social circumstances. Different ICD classification systems are also utilized to document patient treatment and reimbursement, including inpatient hospital care, emergency room care, and outpatient services including clinical and professional services.

The application of natural language processing tools to ICD classification systems provides substantial opportunities for increased efficiency and improved clinical documentation. In addition, ontologically driven NLP processing techniques can be utilized to smooth the transition to newer, more complete coding standards, including implementations of the ICD-10-CM (Clinical Modification) and ICD-10-PCS (Procedure Coding System) standards.

SUMMARY OF THE INVENTION

This application is directed to computer based, ontologically driven systems and methods for procedure coding, including automated ICD and PCS type coding suggestions based on compositional natural language processing (NLP) engines applied to narrative text in the clinical documentation. Software embodiments are also encompassed, including standalone software modules and programs delivered within a computer assisted coding (CAC) platform.

Ontologically driven, compositional NLP analysis can be applied to leverage the properties of multi-axial coding, providing a more comprehensive approach to medical and billing code generation. These techniques can also be designed to support individual coders during the transition from one standard to another (e.g., from ICD-9 to ICD-10-PCS), softening the learning curve and helping to mitigate financial impacts by providing specific coding suggestions based on natural language processing of narrative text and other unstructured data extracted from clinical documentation in medical records.

Semantic objects representing medical codes, rather than medical codes, may be treated as the primitive concepts in the natural language processing system. Thus, partial output (that is, some but not all character slots) may be returned for output, when a full code has not been identified. A full code may not be identified when, for example, at least one slot is provided with a wildcard or other indication that a particular medical concept necessary to specify one or more of the characters was not identified in the narrative text.

BRIEF DESCRIPTION OF THE DRAWINGS

FIG. 7 is a schematic illustration of a workstation-based implementation for the NLP engine of FIG. 6.

DETAILED DESCRIPTION

Figure 1:
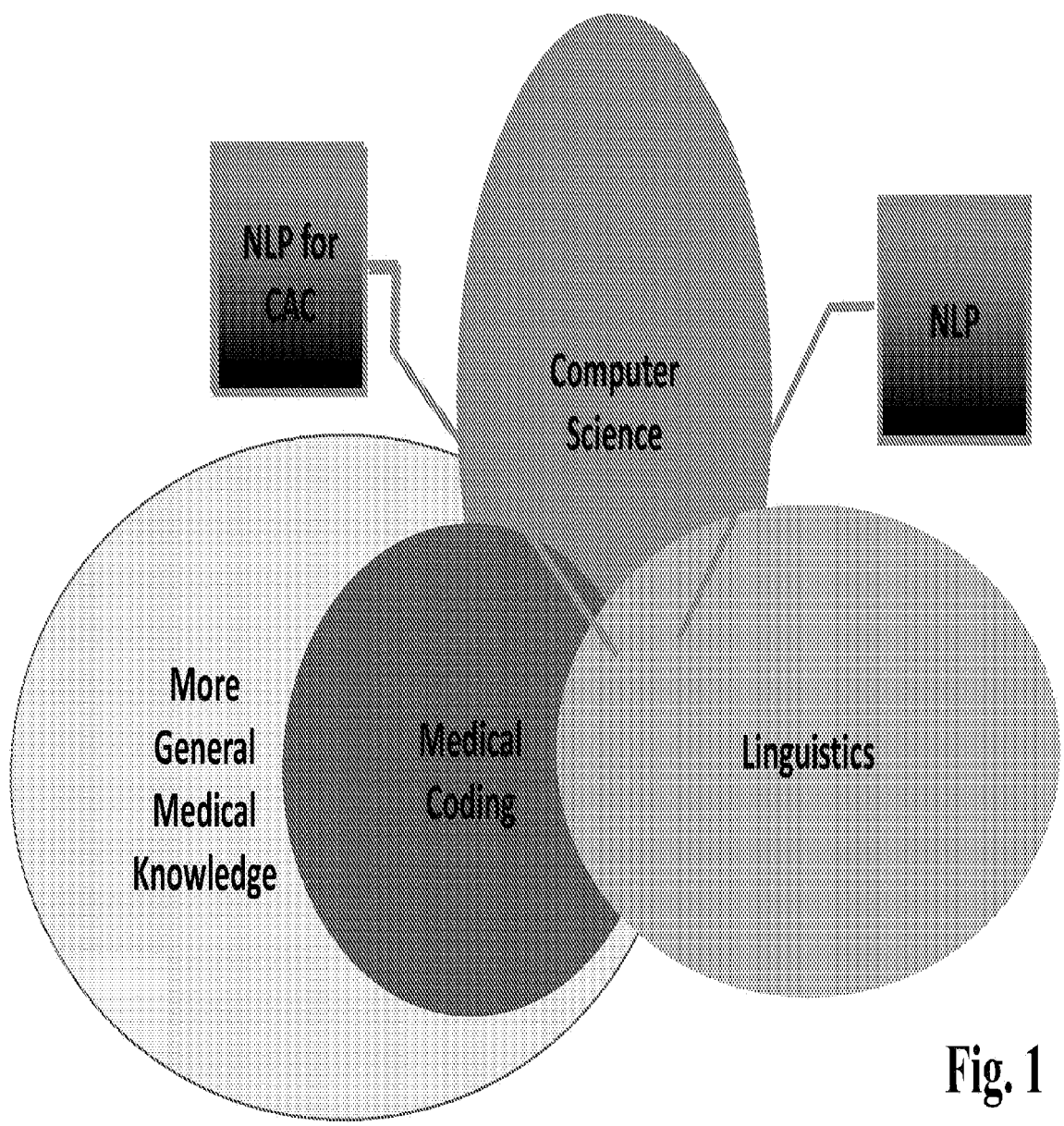
FIG. 1 is a schematic overview illustrating the role of natural language processing in computer-assisted medical coding.

Based on current CMS (Centers for Medicare and Medicaid Services) policy under the Health Insurance Portability and Accountability Act of 1996 (HIPAA), ICD-10 codes will be required for medical care transactions beginning Oct. 1, 2014. Regardless of the actual implementation date, however, the transition to ICD-10-CM/PCS will have a significant impact on U.S. health care payers and providers, particularly with respect to medical record keeping and procedure coding, for both billing and analytical purposes.

ICD-10 is the tenth edition of the International statistical Classification of Diseases and related health problems, and is substantially more comprehensive than the prior version under ICD-9. In fact, ICD-10 actually incorporates two separate coding systems, ICD-10-PCS, the Procedure Coding System for inpatient care (e.g., in hospital settings), and ICD-10-CM (Clinical Modification), a diagnosis coding system that can be used in all U.S. health care settings (e.g., hospitals, clinics, long-term care facilities, etc.).

Generally, diagnosis coding under ICD-10 may utilize parts of the existing MS-DRG (Medicare Severity Diagnosis Related Group) framework, in which services are bundled into DRG codes. Patients may or may not be assigned to the same MS-DRG codes in ICD-9 and ICD-10, however, and there are examples where substantial shifts may occur. PCS coding, on the other hand, is much more specific under ICD-10-PCS, and utilizes a completely different coding format based on a fixed field of seven alphanumeric characters or "slots." There is no simple mapping from the older three-to-five digit system under ICD-9 to the more comprehensive ICD-10 model.

As a result, the ICD-10 coding system is distinct from ICD-9, not merely a revision or extension, and there are a number of potential financial impacts and other industry concerns with respect to implementation. In addition, ICD-10 utilizes significantly more codes than ICD-9, stemming from the more comprehensive approach to diagnostics and procedure coding. A higher degree of specificity and granularity is thus required in the medical record, and coding may be more difficult because individual coders must pay closer attention to clinical details. The likelihood that the reported documentation lacks the detail necessary to justify a given code is also increased. These factors result in loss in productivity, increased claim denial and under-coding, as well as other inefficiencies.

In terms of overall code count, there are almost 72,000 procedure codes currently available under ICD-10-PCS, as compared to approximately 3,900 active ICD-9 procedure codes. This represents an increase of about nineteen times. In addition, individual coders must also adapt to the new structure and organization of the "multi-axial" PCS coding system under ICD-10, in which each of the seven alphanumeric character slots represents a particular component or meaning within the complete code.

In Section 0 of the ICD-10-PCS reference, for example, medical and surgical procedures are indicated by a zero ("0") in slot one. Slot two indicates the body system, and slot three indicates the root operation or procedure that was performed. Slots four and five indicate the body part targeted by the procedure and the approach, respectively. Slot six indicates a device, and slot seven provides a qualifier. Character codes are also provided when the slot is not applicable—for example a "Z" character may indicate that no device is matched to the root procedure, or that there is no qualifier.

Anxieties over the transition to ICD-10 (and other more comprehensive coding systems) include concern about the steep learning curve for medical coders, and potential workforce shortages. Productivity losses are also possible, and under-coding (failure to report billable codes) may be a factor. To address these concerns, ontologically driven, compositional natural language processing is utilized to provide automated coding suggestions, including individual characters in ICD-10-PCS billing codes. Software implementations are provided in standalone form, or delivered within a comprehensive computer assisted coding platform.

These techniques are designed to soften the learning curve during the transition to ICD-10, and also to support coders in ongoing use of the new systems. Automated suggestion and reporting of medical codes (including PCS billing codes) can also help mitigate the financial impact of implementing ICD-10, through more accurate and comprehensive coding, in a manner that leverages the properties of the multi-axial PCS coding system through ontologically driven analysis of the medical record, including compositional natural language processing of narrative text in the clinical documentation.

FIG. 1 provides an overview illustrating the role of natural language processing in computer assisted medical coding. As shown in FIG. 1, natural language processing (NLP) represents an area or subfield within computer science, in particular where computer science intersects with the field of linguistics. Applications of natural language processing (NLP) to computer assisted coding (CAC) lie at the intersection of computer science and linguistics, and within the subfield of medical coding, as defined within the broader field of general medical knowledge.

Natural language processing encompasses a range of computational techniques for analyzing and representing naturally occurring text (e.g., free text in written, narrative, or other descriptive form), for the purpose of achieving human-like language processing for knowledge-intensive applications. Suitable applications include computer assisted coding in the medical field, as shown in FIG. 1. Computer assisted coding, in turn, encompasses the use of computer software to automatically generate or suggest medical codes (or elements within such codes). The suggested coding data are presented for review, validation or use by the coder, based upon review of medical records and other clinical documentation provided by the healthcare practitioners.

Figure 2:
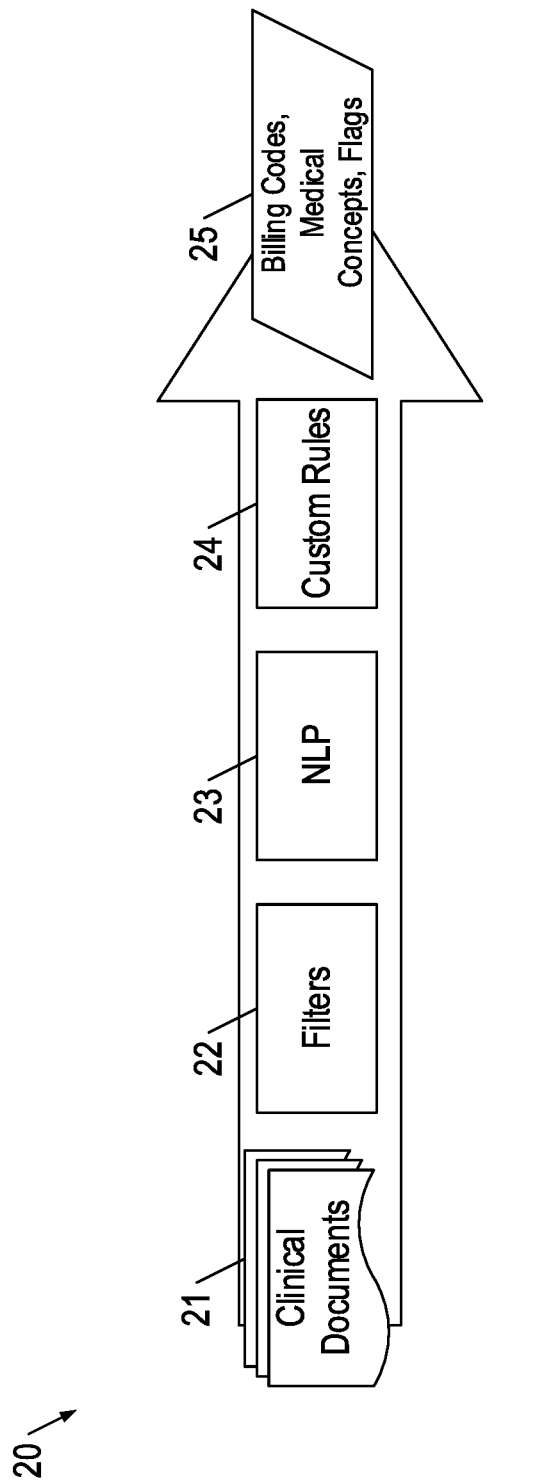
FIG. 2 is a schematic illustration of a procedure coding system or PCS engine for clinical document analysis, using natural language processing.

FIG. 2 is a schematic illustration of a procedure coding system or PCS engine 20, using natural language processing. In this particular example, clinical documents and other medical records 21 are processed using document filters 22 and a natural language processing engine 23. Custom rules 24 are applied in order to generate output 25, utilizing a knowledge base to generate suggested billing codes. Additional output 25 can also be generated, for example medical concepts or other evidence used to fill one or more character fields or slots within a billing code, or to flag a record for additional provider input.

Document filters 22 are configured to identify document types, and to identify narrative text and other segments or sections of words within particular documents 21 for natural language processing. Natural language processing engine 23 is configured to map the narrative (or free text) to medical concepts, medical codes, and data fields or slots within medical codes, preserving links to the relevant text. Customized rules 24 provide for universal and application-based (customer-specific) post-processing of the suggested codes and field data.

Figure 3:
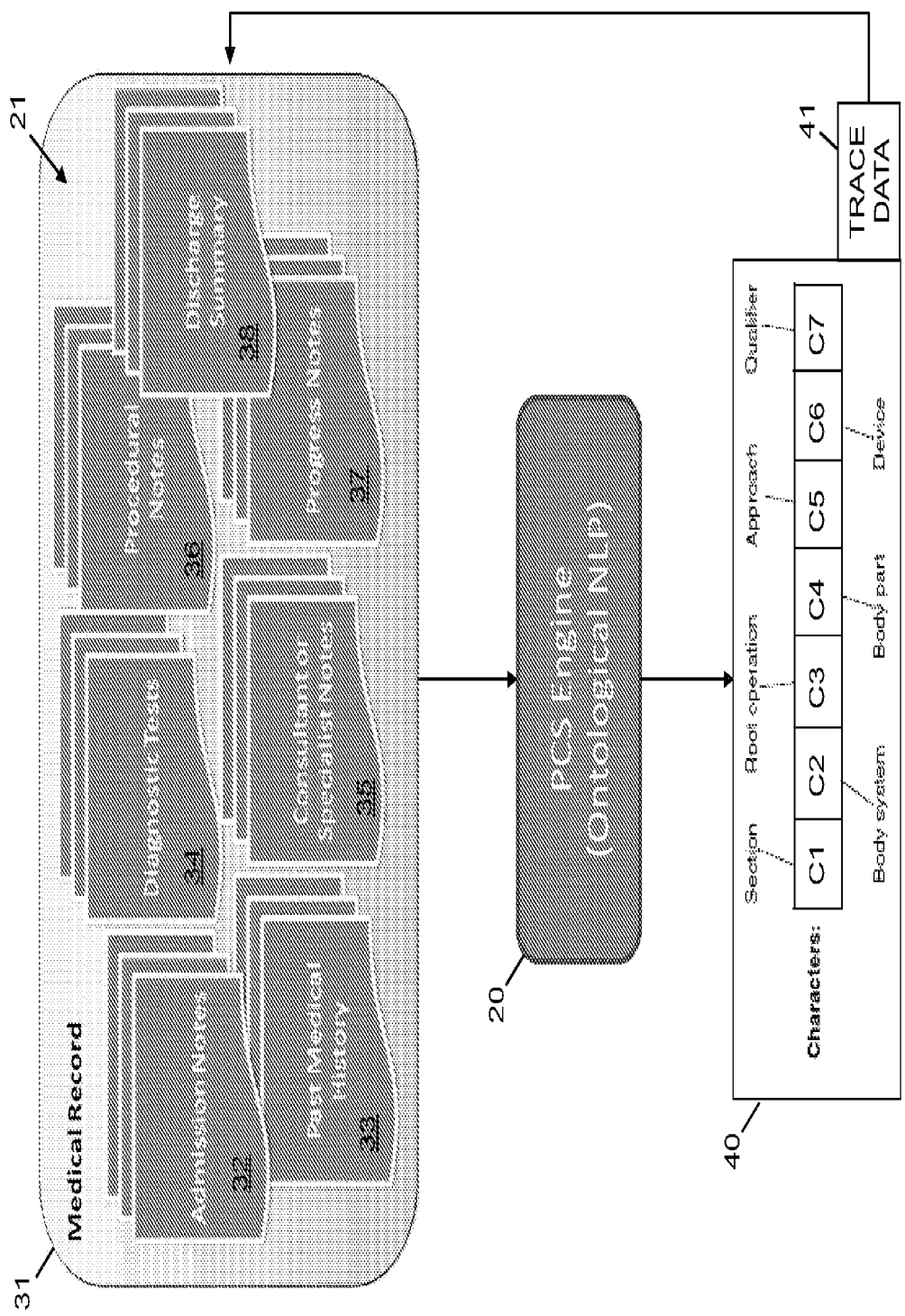
FIG. 3 is a block diagram illustrating operation of a natural language based procedural coding system.

FIG. 3 is a block diagram illustrating operation of PCS engine 20 on representative clinical documents 21 in a medical record 31. In this example, documents 21 serve as input to PCS engine 20, which generates output in the form of characters or other elements C1-C7 within a particular medical code 40.

Representative documents 21 in medical record 31 include, but are not limited to, admission notes 32, medical histories 33, diagnostic tests 34, consultant or specialist notes 35, procedural notes 36, progress notes 37, and discharge summaries 38. Depending on the application, there may be fewer or more categories of individual documents 32-38, and clinical records 21 can be organized differently within any given medical record 31. Clinical documentation 21 may also include additional data such as blood tests and other lab results, x-rays, computer-assisted tomography (CAT) and magnetic resonance imaging (MRI) scans and other images, electrocardiogram (ECG or EKG) and EEG (electroencephalogram) data, operating room notes (ORN), medical histories, observational notes, and other medical and clinical records.

Generally, clinical documentation 21 and medical records 31 include both structured and unstructured data. Unstructured data includes narrative text, free text, descriptions, notes, and summaries, as provided by a physician or other caregiver (or by the patient), for example in admission notes 32, histories 33, consultant or specialist notes 35, procedural notes 36, progress notes 37, and discharge summaries 38, or in the form of free text associated with imaging or diagnostic testing 34. Diagnosis and treatments codes can also be considered structured data, as well as medication orders. Structured and semi-structured data, on the other hand, typically have more particular schemes and formats, for example lab results and "pick-list" or drop down menu items selected from a limited number of fields.

PCS engine 20 extracts narrative text from clinical documents 21, segments the narratives and tokenizes and parses the segmented text into sequences of words, phrases, and sentences, which are mapped to corresponding semantic objects in the ontology database. In particular, the ontology defines hierarchically organized classes of objects which correspond to (or mirror) the multi-axial coding system of code 40, for example character slots C1-C7 in the ICD-10-PCS coding scheme, as shown in FIG. 3.

Additional trace data 41 can also be provided, linking code 40 and its primitive elements C1-C7 back to particular locations within documents 21, where the supporting text (words, phrases and sentences) can be found. Trace data 41 can be used for auditing and verification purposes, for example to help the coder determine whether to approve or discard a suggested code 40, or to assist the coder in locating additional text and other (structured or unstructured) data in medical record 30, needed to fill in any missing characters and complete code 40.

In the ICD-10-PCS scheme, each character's position or slot can be understood as a semi-independent axis of classification, which allows different specific values to be inserted into a particular space within a given code 40, and whose physical position (or slot number) remains stable. Within a defined code range (e.g., in medical and surgical section 0, character C1), the characters retain the same general meaning that they would confer on any code value, in the given position.

The concept of body part, for example (character C4), may relate to a kidney or ureter (or both), each of which is in turn associated with a laterality (e.g., on the left side). The multi-axial system is hierarchical, in that identification of a kidney or ureter is associated with the higher-order urinary system (character C2), and with various root operations or core procedures such as resection (character C3), each having a range of different potential approaches (e.g., open or percutaneous endoscopic, character C5). Additional fields or characters can also be included, for example fusion of the C-4/5 vertebral joint with a fixation device (character C6), or a qualifier (character C7) such as diagnostic or stereotactic.

Figure 4:
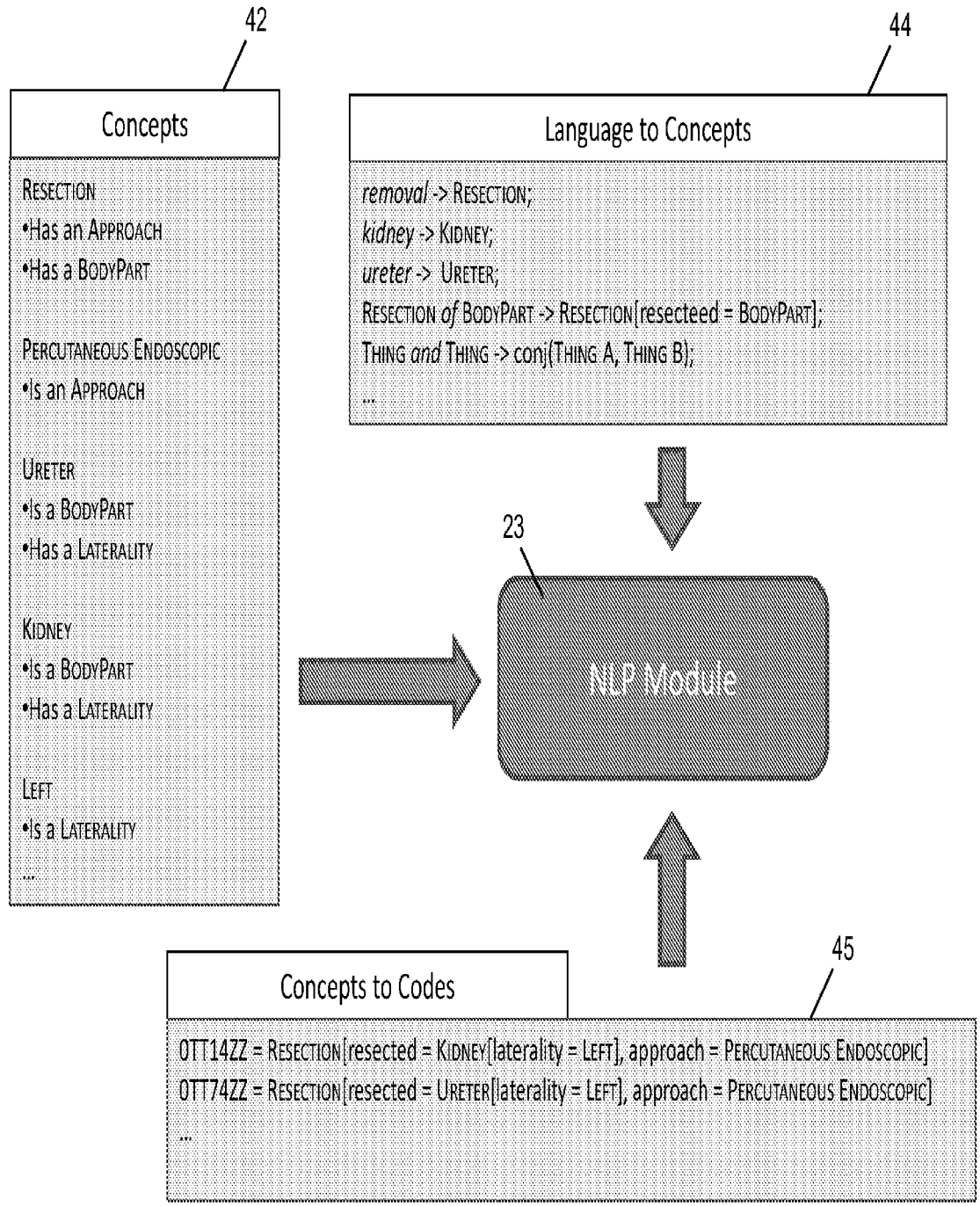
FIG. 4 is a schematic illustration of a natural language based PCS engine application.

FIG. 4 is a schematic illustration of a representative application for a procedure coding system, for example utilizing NLP module 23. As shown in FIG. 4, NLP module 23 operates on conceptual data 42 related to the renal system, applies a language-to-concept oriented processing or mapping 44 to the input documentation, and then expresses its findings as PCS codes using the concepts-to-codes mapping 45.

Conceptual data 42 were developed as a component of the PCS engine and are stored in a proprietary, ontological knowledge base format for use in medical NLP. The conceptual data is developed by research linguists and subject matter experts. It is a knowledge base (data source) that the PCS modules and algorithms utilize. In embodiments, it is the ontology. The PCS engine maps narrative text into these knowledge base concepts.

In this example of a renal system application, relevant concepts include resection, which implies a body part and approach, and ureter and kidney concepts which are body parts with laterality specifications. These concepts are hierarchically organized within the system's ontology, and relate to the multi-axial coding scheme as described above.

Language-to-concept mapping 44 is also based on natural language processing. In this particular case, some of the matching is straightforward, for example kidney/kidney and ureter/ureter, but the natural language approach also encompasses synonymy, hyponymy, hypernymy, paraphrase and context-based matching based on the subject matter of the record, for example identifying the more informal term "removal" with the surgical procedure of resection. Additional higher-order language-to-concept matching 44 is also encompassed, including matching laterality of the resected body parts (e.g., kidney and ureter), and more generalized conjunctive mappings of related syntactic concepts or other higher-order data structures.

PCS codes are output using the concepts-to-codes data resource 45, following the conceptual mapping. In ICD-10 applications, resolution of the code-based output can be directly related to the multi-axial (field slot-based) PCS coding scheme. For example, surgical resection of the left kidney via a percutaneous endoscopic procedure is processed to generate ICD-10-PCS code 0TT14ZZ, and resection of the left ureter generates code 0TT74ZZ.

Figure 5:
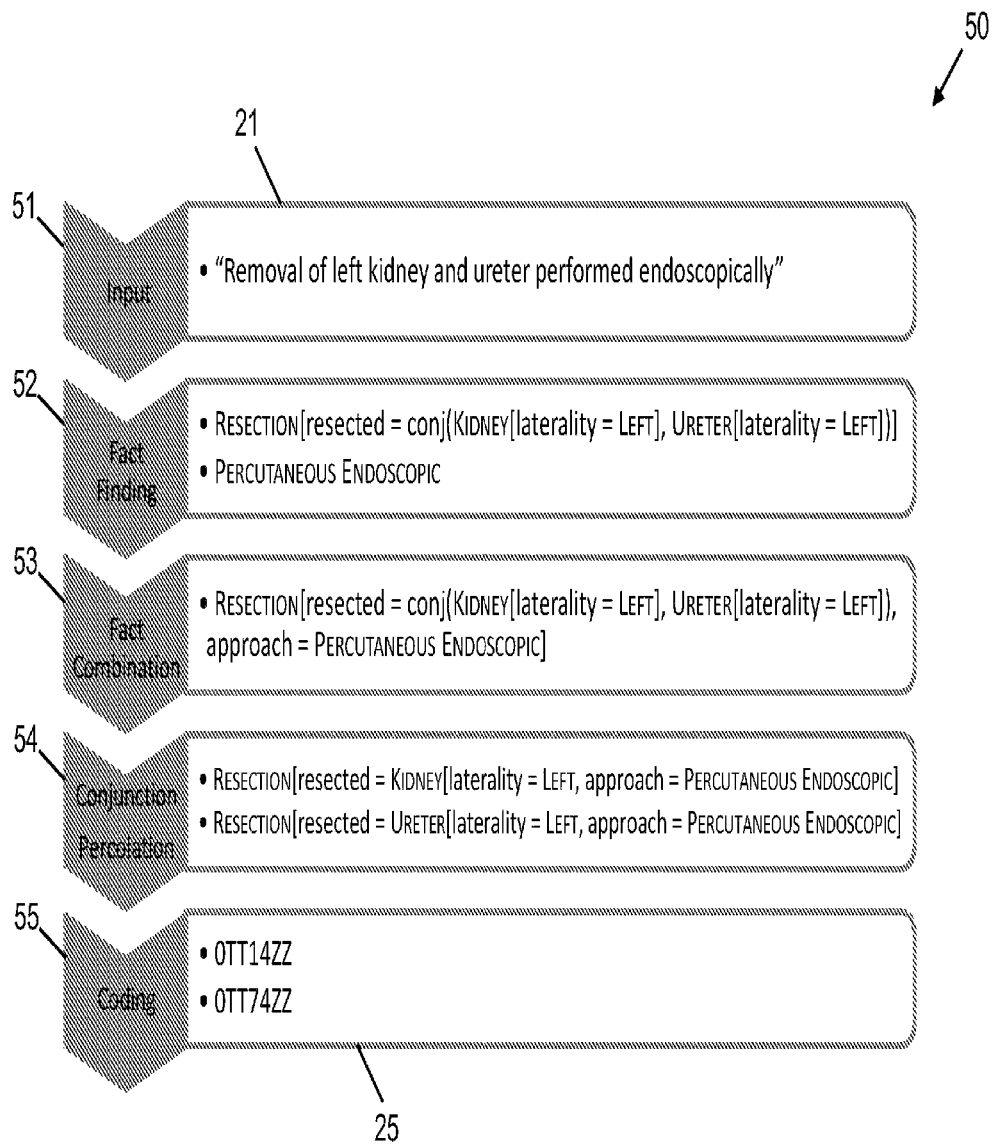
FIG. 5 is a block diagram of a natural language based method for procedure coding.

FIG. 5 is a schematic overview of a natural language based method for procedure coding as applied to the renal system example of FIG. 4, above. In this particular embodiment, method 50 includes input (step 51), fact finding (step 52), fact combination (step 53), conjunction percolation (step 54), and coding (step 55).

Input (step 51) is directed to input of (e.g., unformatted) data extracted from a particular clinical record 21, in this case "Removal of left kidney and ureter performed endoscopically," as show in FIG. 5. For this example, the input data are segmented at the sentence level, and then parsed for additional processing.

Fact finding (step 52) is directed to matching words (or other elements) in the input text to relevant concepts, utilizing a language-to-concept mapping 44 as described above. In this particular example, "removal" is matched to the root operation or core procedure "resection," and "performed endoscopically" is matched to "percutaneous endoscopic."

Fact combination (step 53) generates higher-order combinations or conjunctions of the relevant facts and concepts. In this example, the "percutaneous endoscopic" object is identified as the approach of the "resection" object.

Conjunction percolation (step 54) removes any explicit conjunction by cloning and modifying.

Coding (step 55) generates the elements of one or more comprehensive medical codes. In ICD-10-PCS, for example, the overall context is defined by the medical and surgical procedure section (first character or slot "0"), and the kidney and ureter are associated with the urinary system (second character "T"). Resection is also coded with the character "T," this time appearing the third slot.

For percutaneous endoscopic resection of both the kidney and ureter, two separate codes are generated as output 25. In the urinary system, the left kidney codes as "1" (fourth character, first code), and the left ureter codes as "7" (fourth character, second code). Both procedures are performed via the percutaneous endoscopic approach (fifth character "4"), and there is no device or qualifier (six and seventh characters are both "Z").

Thus, natural-language processing based method 50 for procedure coding generates two complete ICD-10-PCS codes, based on a single-sentence entry in the clinical documents. The task of the coder, then, is to verify the suggested fields, and approve the code for entry. In other examples, data from multiple documents is combined to generate the coded output, and in some cases not all the characters or slots can be populated. When this occurs, the coder can be prompted to search for additional data in the record, or to generate a physician inquiry in order to complete the documentation at the provider end.

Figure 6:
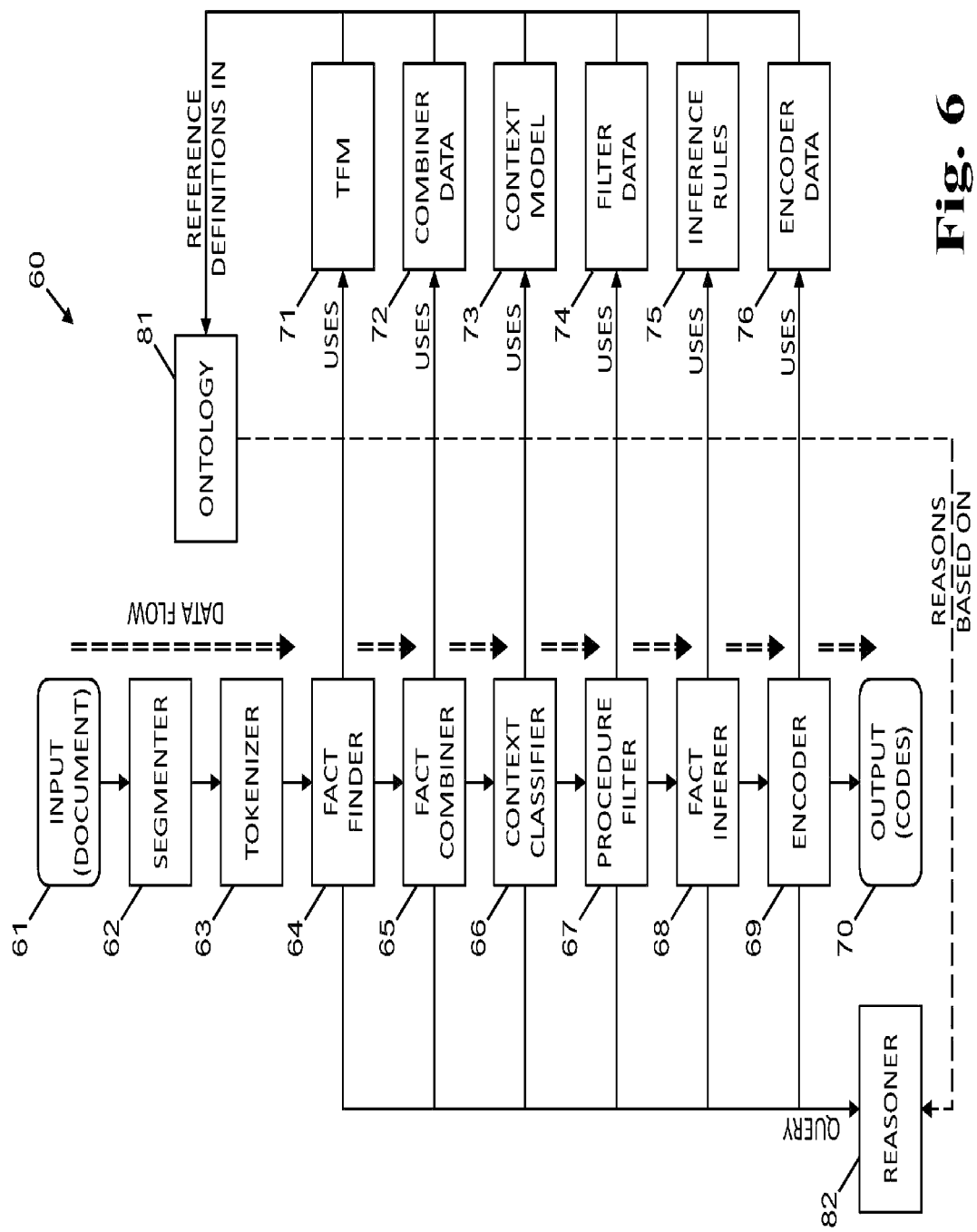
FIG. 6 is a block diagram of an ontologically driven, natural language processing (NLP) engine for medical coding.

FIG. 6 is a block diagram illustrating natural language processing engine 60 for medical coding, with an ontology driven architecture. Engine 60 represents NLP component 23 of FIG. 2, as embodied in a computer system configured by executable software code to perform natural language based, ontologically driven medical coding procedures as described herein.

As shown in FIG. 6, NLP engine 60 acts on input 61 including unformatted narrative text and other data from clinical documentation including, but not limited to, hospital inpatient records utilized for PCS coding. Engine 60 utilizes a number of software or processing (NLP) modules to generate output 70 from input documentation 61, for example one or more of segmenter 61, tokenizer 62, fact finder 64, context classifier 66, procedure filter 67, fact inferrer 68 and encoder 69. The processor modules utilize a number of knowledge base resources (or databases), for example one or more of text-to-fact map (TFM) 71, combiner data 72, context model 73, filter data 74, inference rules 75, and encoder data 76.

In embodiments, concepts-to-codes data resource 45 of FIG. 4 may correspond to an encoder data resource 76 of FIG. 6. Similarly, conceptual data resource 42 of FIG. 4 may correspond to an ontology resource (or database) 81, and language-to-concept data resource 44 of FIG. 4 may correspond to a text-to-fact map (TFM) 71 of FIG. 6, respectively.

Ontology database 81 is a core data resource, which defines the categories of objects (processes, entities and their attributes) relevant to the coding system, along with various relationships among these objects. Knowledge base resources 71-76 reference the definitions in ontology resource 81, with text-to-fact map (TFM) 71 to express how particular language within documentation 61 is used to refer to the different classes of objects described in ontology resource 81. Selected NLP modules 64-68 direct queries to reasoner module 82, which utilizes reasoning that is also based on ontology resource 81.

The functioning of the processor modules in NLP engine 60 is guided by the extensive knowledge base resources 71-76 and 81, including information pertaining to the language and terminology of clinical documentation, medical coding guidelines and logic, and the structure and content of the PCS coding system itself. As shown in FIG. 6, for example, NLP engine 60 utilizes nine software-based processors (or NLP modules) 62-69 and 82, and seven knowledge base resources (or databases) 71-76 and 81. The number of processing modules and knowledge base resources varies, however, based on content of input documentation 61 and the desired format of coding data and other output 70. Even within a given coding system, moreover, the processor modules and corresponding knowledge base resources can also be arranged and combined in a variety of different ways along the data stream, in order to suit particular coding needs.

In PCS and other advanced coding applications, output 70 can be provided in the form of an extensible markup language (XML) file, or other suitable data format. For the specific purpose of PCS coding, output 70 identifies primitive medical concepts based on input documentation 61, for example sections, body systems, root operations, core procedures, body parts, laterality, approaches, devices, qualifiers, diagnoses, and specifications, and the associated PCS billing codes they support, as defined within the context of documentation 61.

Output 70 also includes trace information defining relationships between the identified medical concepts and corresponding locations in documentation 61, providing a link or mapping back to the data in the record that supports each of the identified concepts, and the corresponding elements (characters or slots) within the associated or suggested PCS billing codes. The trace data provide an audit trail for determining how particular codes are assigned to output 70, and allow for verification of the relationship between particular codes and the corresponding supporting data, as located in input documentation 61.

In operation of NLP engine 60, narrative text is input to segmenter module 62, which delimits the text into sections of words based on the formatting and content of documentation 61. Example sections include "Chief Complaint," "History of Present Illness" and "Diagnosis," among others. Segmentation provides for more accurate PCS coding, because human medical coders may not necessarily code based on content in all sections of a given document, and the sections in which evidence for a particular code is found may be pertinent to the logic that defines the final list of PCS coding data and other output 70 that is sent on for billing and analysis.

Segmented text generated by segmenter 62 is transmitted to and received by tokenizer module 63. Tokenizer 63 generates a sequence of items based on the segmented text and corresponding boundaries in the clinical documentation, where the items are (or represent) individual words, sentence boundaries and section boundaries. The words are the raw data from which medical concepts in ontology resource 81 are identified, while the sentence and section boundaries help identify the contexts in which multiple words and other tokenized objects can be considered together in forming more complex medical and billing code concepts.

The next two modules, fact finder 64 and fact combiner 65, are responsible for mapping the output of tokenizer 63 into semantic objects and relationships defined in the ontology, for example via text-to-fact map (TFM) 71. Ontology resource (or database) 81 includes hierarchically organized classes of objects. These objects correspond in granularity and organization to the axes of the PCS standard, but as primitive medical concepts are applicable to other medical coding schemes. Fact combiner 65 also utilizes combiner data 72.

Within PCS section 0, hierarchies of body part classes exist in correspondence to character slot 4, and hierarchies of procedural approach classes exist in correspondence to character slot 5. Mirroring this multi-axial PCS coding system within ontology 81 allows NLP engine 60 to compositionally identify core semantic elements of the different PCS codes, either in addition to or in place of a fully specified PCS code (for example, in cases where input documentation 61 is deficient, and a complete code cannot be defined).

Ontology 81 also specifies relationships between semantic classes, such as identifying body parts for which the attribute of laterality is relevant (e.g., left, right, bilateral, or unilateral), and which medical devices are relevant to which core procedures. This information allows NLP engine 60 to more accurately combine the core components of meaning (e.g., semantic objects) into more complex concepts, and ultimately to generate more appropriate PCS characters and codes. NLP engine 60 also generates trace data connecting the elements of output 70 to specific locations in input documentation 61, where supporting narrative text or other data can be found in the medical record.

Output from fact combiner 65 is processed by context classifier 66 and procedure filter 67. These modules work to refine the collection of ontological objects and the relationships between them in accordance with their linguistic context, as well as coding logic and guidelines.

Context classifier 66 identifies properties of an object's context that may indicate whether the object should or should not be converted into a component of a PCS code for billing or analysis. Examples include identifying negated contexts, e.g., in which an identified procedure was not performed on a particular patient, and past contexts, e.g., in which the procedure was performed on the patient, but as an aspect of a prior encounter, not the current encounter.

While other elements of NLP engine 60 make use of symbolic natural language processing driven by linguist and coder defined terminology, concepts, relationships and rules, context classifier 66 also employs machine learning. Specifically, context classifier 66 is trained using sample clinical documentation in which relevant medical concepts and associated PCS codes have been identified, in order to learn what terminology and contextual properties are pertinent to the relevance of a particular concept in final system output 70, for example as defined in context model 73. This methodology distinguishes from other computer assisted coding solutions, in that symbolic natural language processing is used to generate (or over-generate) medical concepts from input documentation 61, and machine learning techniques are employed to prune the results and remove particular concepts based on contextual information including negated and past contexts.

Procedure filter module 67 applies rules reflecting medical coding guidelines to further prune the results. For example, guideline logic may indicate that although two procedures are performed, only one may be reported for billing purposes. In this case, one procedure may be considered an inherent aspect of the first, as defined by filter database resource 74.

Filtered output from PCS filter 67 is passed to fact inferrer 68, which identifies additional information not directly or expressly stated in documentation 61, but reasonably and compliantly inferred. Examples may include, for example, body system character codes based on body part and root operation or core procedure data, as defined within inference rules resource 75, where the corresponding semantic objects may not necessarily map to express text in the clinical documentation.

Semantic objects identified in or inferred from the data stream are transmitted to encoder module 69, which converts the identified objects into medical coding data for output 70. When documentation 61 is sufficiently specific, complete medical and billing codes can be generated, along with tracing data relating each of the individual character slots to particular locations in documentation 61. When the documentation is incomplete, on the other hand, encoder 69 can still map specific axes of the semantic object onto appropriate positions or slots in a partially specified code.

When NLP engine 60 is able to confidently identify some but not all of the seven characters in a PCS code, therefore, a partially specified code can be generated, in which the known characters are provided and the unidentified content is marked with a wild card or other flag. For example, the fully specified PCS code for "open approach abdominal wall drainage" is 0W9F0ZZ, whereas the output for this procedure may be 0W9F_ZZ when the approach (character slot 5) cannot be identified. This code indicates "abdominal wall drainage, approach not specified," with the underscore ("_") representing the wildcard or other incomplete coding flag associated with the selected slot, for which there is no corresponding semantic object mapped to text in the medical documentation.

This distinguishes from other "all or nothing" computer assisted coding systems, in which each code is treated as a primitive, rather than the individual characters or slots within the code, and in which the system cannot report a partially specified code, so little or no information is provided unless the entire code is identified. NLP engine 60, in contrast, is configured to provide useful output 70 even when all the content of a particular code cannot be recognized or inferred from input documentation 61. In particular, NLP engine 60 can fill in some or most of the code slots or characters automatically, based on the ontological (NLP) analysis of documentation 61, and provide wildcard characters or other flags for completion by the (human) medical coder, for example using an auto-suggested completion tool.

Alternatively, a physician inquiry or message can be generated, in order to alert others to the need for more complete clinical data in a given medical record. During the transition to ICD-10-PCS, for example, clinical documentation may initially be lacking in the degree of specificity required to identify all of the complete PCS codes, whether intended for actual billing or analysis purposes. In addition to suggesting codes to complete these cases, therefore, NLP engine 60 can also guide the provider to improved documentation practices, and identify areas where greater specificity is required at the provide end, for a more comprehensive, accurate and supportable clinical recordkeeping and coding process.

In general, moreover, the bulk of information pertinent to any specific coding system can also be provided by encoder database 76 and handled by encoder 69, so that "upstream" processing modules 62-68 and supporting knowledge base resources 71-75 are substantially coding system independent. Thus, NLP engine 60 can be adapted to a broad range of different coding systems based on suitable modifications of encoder module 69 and corresponding database resource 76 (and ontology 81), including not only procedure-based coding under ICD-10-PCS, but also diagnosis based Clinical Modification coding under ICD-10-CM, DRG (Diagnosis Related Group) and MS-DRG (Medicare Severity Diagnosis Related Group) coding, SNOMED, and CPT (Current Procedural Terminology) coding for medical, surgical, and diagnostic services, or any other coding system that is based on medical concepts.

FIG. 7 is a schematic illustration of a workstation-based system 90 for implementing an ontologically driven, natural language processor based medical coding system, for example NLP engine 60 of FIG. 6. In this particular embodiment, a coder or other user 91 is provided with workstation 90 including graphical user interface 92 in communication with memory and processor components 93. Memory and processor components 93 are configured to operate NLP engine 60, for example by executing suitable NLP engine software stored on a non-transitory computer readable medium.

Generally, NLP engine 60 can be provided as a standalone software-enabled processing system or method, or within a computer assisted coding platform. Input is provided in the form of medical records 61 stored in medical records database 94, either locally within workstation 90, or retrieved from a clinical server or other resource via a secure network or cloud-based communication link.

Output 70 is provided on graphical user interface (GUI) 92. User interface 92 is configured for interaction with a coder 91 in order to select or reject suggested medical and billing codes, complete individual code elements flagged by wildcard characters. User interface 92 is also configured for auditing and verification operations based on trace data relating the code elements (e.g., slots or characters) to particular locations in documentation 61, and the corresponding narrative. Additional output 95 can thus be provided in the form of audit results and other reporting, including physician inquiries based on incomplete clinical documentation 61, and other output for clinical documentation improvement (CDI).

In operation of workstation system 90, clinical documentation 61 from database 94 is delivered as input to NLP engine 60, from which narrative text is read and processed to generate suggested PCS codes and other output 70 on graphical user interface 92 of workstation 90. Output 70 may be generated in fully coded or partially specified form, based on the completeness of documentation 61, and the ability of NLP engine 60 to extract the required information.

Medical coders and other users 91 can review output 70 in an auditing capacity, for example using GUI 90 to review selected documentation 61 based on the trace data. As necessary and appropriate, users 91 may also accept, edit or delete the suggested medical and billing codes, or even add codes that were not suggested by NLP engine 60, for example based on review of additional clinical documentation 61. Users 91 can also complete character slots or other fields in any partially specified codes proposed by NLP engine 60. The collection of codes and any other user output 95 is then sent to billing or reported for analysis, along with any physician inquiries, turnbacks, and other clinical documentation improvement related data.

In some embodiments, the creation of semantic objects (and other semantic representations of input documentation 61) may be considered an intermediate step. In this approach, NLP engine 60 can be configured to map directly from input text to PCS coding data and other output, for example using a machine-learning algorithm.

NLP engine 60 thus provides a range of features that are not found in other computer assisted coding systems, including, but not limited to:

Providing a semantic ontology that includes hierarchically organized classes of medical concepts, and which represents the relationships between these concepts in a manner that reflects the multi-axial organization of the PCS coding system.

Driving accurate and comprehensive coding, using an ontology that enables recognition of PCS codes and other complex concepts from the composition of more primitive elements of meaning (e.g., character slots), and constrains the composition of full codes based on the corresponding ontology.

Enabling partially specified PCS (and other) coding output, adding substantial value to computer assisted coding software-based systems and methods.

Separating the primary NLP processing and related ontology of generalized medical concepts from the specifics of any particular coding system, making the engine readily adaptable to other coding systems such as ICD-10 CM, CPT, SNOMED, etc.

Facilitating modular (and hence rapid) knowledge base development, utilizing dedicated (modular) databases corresponding to each step (and NLP module) in the natural language processing chain.

Additional features provide for the production of partially specified codes when clinical documentation is lacking in the specificity required to fully support a given code, and flagging missing information using a wildcard or other indicator for follow up when required information is absent from the clinical documentation, or when it is missed by one or more of the upstream NLP modules. Thus, the suggested codes need not be all or nothing, with trace information to support clinical documentation improvement (CDI).

Auto-completion functionality can also be enabled, in order to streamline the medical coding process even when not all information is available or identified within the input documentation. The integration of rule-based (symbolic) natural language processing and machine learning approaches also allows for the original sets of medical concepts and procedures to be refined before final coding, utilizing contextual cues and linguistic and coding logic to reject negated or past procedure information as appropriate before billing codes and other output data are generated.

Utilization of a grammar-based text-to-fact mapping provides for recognizing both individual words and multi-word phrases for conversion into a network of semantic objects. This use of grammar in processing text from the clinical record also allows for greater precision than in other approaches, for example utilizing word order to validate the medical concepts underlying suggested codes and providing trace data by citing the particular words and phrases that generated matches in the grammar-based mapping. Mapping the parsed text onto semantic objects also makes it possible for the remainder of the NLP engine processing to be directed by the ontology, rather than utilizing an ad hoc mapping or other non-ontological procedure.

While this invention has been described with reference to exemplary embodiments, it will be understood by those skilled in the art that various equivalents may be substituted and different changes and modifications can be made to adapt these teachings to particular problems, situations and materials, without departing from the spirit and scope of the invention. The invention encompasses all the different embodiments falling within the scope of the appended claims, and is not limited to the particular examples that are disclosed.

The invention claimed is:

1. A computer-implemented method comprising:
receiving, by one or more processors, clinical data comprising narrative text;
identifying, by the one or more processors, one or more sequenced words within the narrative text;
mapping, by the one or more processors, each of the one or more sequenced words to one or more semantic objects of an ontology, wherein (a) the ontology defines classes of the one or more semantic objects corresponding to axes of a multi-axial coding scheme, (b) the ontology defines concepts of a conceptual data resource, (c) the classes of the one or more semantic objects define a hierarchical structure in the ontology, and (d) the hierarchical structure defines relationships between the one or more semantic objects;

converting, by the one or more processors, the one or more semantic objects into one or more characters;

generating, by the one or more processors, a partial code by, at least in part, outputting the one or more characters into one or more slots based at least in part on the multi-axial coding scheme, wherein (a) the partial code comprises at least one blank slot, and (b) in the multi-axial coding scheme, each position of a character within the partial code corresponds to a semi-independent axis of classification;

outputting, by the one or more processors, an inquiry requesting clinical documentation comprising additional unstructured data embodied as narrative text, based at least in part on the at least one blank slot, wherein outputting an inquiry comprises generating a suggestion for the additional unstructured data to provide greater specificity to the clinical data and comprises providing the suggestion with the request;

responsive to receiving the clinical documentation comprising the additional unstructured data, mapping, via natural language processing and by the one or more processors, at least a portion of the additional unstructured data to at least one additional semantic object of the ontology;

converting, by the one or more processors, the at least one additional semantic object into at least one additional character; and generating, by the one or more processors, a complete code by, at least in part, outputting the at least one additional character into the at least one blank slot.

2. The computer-implemented method of claim 1, wherein the clinical data comprises clinical documentation comprising narrative text.

3. The computer-implemented method of claim 1, wherein the clinical data comprises unstructured data.

4. The computer-implemented method of claim 1, wherein the hierarchical structure defines relationships among the one or more characters in the one or more slots based at least in part on the multi-axial coding scheme.

5. The computer-implemented method of claim 1, further comprising outputting trace data including linking information to map characters in a selected slot of the one or more slots to particular portions of the narrative text of the clinical data.

6. The computer-implemented method of claim 3, wherein the inquiry requesting clinical documentation comprising additional unstructured data is output based at least in part on the relationships among the one or more characters in the one or more slots based at least in part on the multi-axial coding scheme.

7. A computer system comprising:
a database comprising memory for storing clinical data; and
one or more computer processors operatively coupled to an interactive display and in communication with the database, the one or more computer processors configured to:
receive clinical data comprising narrative text;
identify one or more sequenced words within the narrative text;
map each of the one or more sequenced words to one or more semantic objects of an ontology, wherein (a) the ontology defines classes of the one or more semantic objects corresponding to axes of a multi-axial coding scheme, (b) the ontology defines concepts of a conceptual data resource, (c) the classes of the one or more semantic objects define a hierarchical structure in the ontology, and (d) the hierarchical structure defines relationships between the one or more semantic objects;

convert the one or more semantic objects into characters;

generate a partial code by, at least in part, outputting the one or more characters into one or more slots based at least in part on the multi-axial coding scheme, wherein (a) the partial code comprises at least one blank slot, and (b) in the multi-axial coding scheme, each position of a character within the partial code corresponds to a semi-independent axis of classification;

output, an inquiry requesting clinical documentation comprising additional unstructured data embodied as narrative text, based at least in part on each of the at least one blank slot, wherein outputting an inquiry comprises generating a suggestion for the additional unstructured data to provide greater specificity to the clinical data and comprises providing the suggestion with the request;

responsive to receiving the clinical documentation comprising the additional unstructured data, map, via natural language processing, at least a portion of the additional unstructured data to at least one additional semantic object of the ontology;

convert the at least one additional semantic object into at least one additional character; and generate a complete code by, at least in part, outputting the at least one additional character into the at least one blank slot.

8. The computer system of claim 7, wherein the clinical data comprises clinical documentation comprising narrative text.

9. The computer system of claim 7, wherein the clinical data comprises unstructured data.

10. The computer system of claim 7, wherein the hierarchical structure defines relationships among the one or more characters in the one or more slots based at least in part on the multi-axial coding scheme.

11. The computer system of claim 7, wherein the computer processor is further configured to output trace data including linking information to map characters in a selected slot of the one or more slots to particular portions of the narrative text of the clinical data.

12. The computer system of claim 9, wherein the inquiry requesting clinical documentation comprising additional unstructured data is output based at least in part on the relationships among one or more characters in the one or more slots based at least in part on the multi-axial coding scheme.

13. A non-transitory computer-readable storage medium having program code embedded thereon, the program code executable on a processor of a computer system to perform processes for:
receiving clinical data comprising narrative text;
identifying one or more sequenced words within the narrative text;
mapping each of the one or more sequenced words to one or more semantic objects of an ontology, wherein (a) the ontology defines classes of the one or more semantic objects corresponding to axes of a multi-axial coding scheme, (b) the ontology defines concepts of a conceptual data resource, (c) the classes of the one or more semantic objects define a hierarchical structure in the ontology, and (d) the hierarchical structure defines relationships between the one or more semantic objects;

converting the one or more semantic objects into characters;

generating a partial code by, at least in part, outputting the one or more characters into one or more slots based at least in part on the multi-axial coding scheme, wherein (a) the partial code comprises at least one blank slot, and (b) in the multi-axial coding scheme, each position of a character within the partial code corresponds to a semi-independent axis of classification;

outputting an inquiry requesting clinical documentation comprising additional unstructured data embodied as narrative text, based at least in part on the at least one blank slot, wherein outputting an inquiry comprises generating a suggestion for the additional unstructured data to provide greater specificity to the clinical data and comprises providing the suggestion with the request;

responsive to receiving the clinical documentation comprising the additional unstructured data, mapping, via natural language processing, at least a portion of the additional unstructured data to at least one additional semantic object of the ontology;

converting the at least one additional semantic object into at least one additional character; and generating a complete code by, at least in part, outputting the at least one additional character into the at least one blank slot.

14. The non-transitory computer-readable storage medium of claim 13, wherein the clinical data comprises clinical documentation comprising narrative text.

15. The non-transitory computer-readable storage medium of claim 13, wherein the clinical data comprises unstructured data.

16. The non-transitory computer-readable storage medium of claim 13, wherein the hierarchical structure defines relationships among the one or more characters in the one or more slots based at least in part on the multi-axial coding scheme.

17. The non-transitory computer-readable storage medium of claim 13, further executable on a processor of a computer system to perform processes for: outputting trace data including linking information to map characters in a selected slot of the one or more slots to particular portions of the narrative text of the clinical data.

18. The non-transitory computer-readable storage medium of claim 15, wherein the inquiry requesting clinical documentation comprising additional unstructured data is output based at least in part on the relationships among one or more characters in the one or more slots based at least in part on the multi-axial coding scheme.

* * * * *